United States Patent
Brain

[11] Patent Number: 6,055,984
[45] Date of Patent: May 2, 2000

[54] ENDOTRACHEAL TUBE CONSTRUCTION

[76] Inventor: Archibald I. J. Brain, Sandford House, Fan Court Gardens, Longcross Road, Chertsey, Surrey KT16 0DJ, United Kingdom

[21] Appl. No.: 08/964,664

[22] Filed: Nov. 5, 1997

[30] Foreign Application Priority Data

Nov. 6, 1996 [GB] United Kingdom .................... 9623060
Feb. 24, 1997 [GB] United Kingdom .................... 9703764

[51] Int. Cl.$^7$ .................................................. A61M 16/00
[52] U.S. Cl. .................................. 128/207.14; 128/207.15
[58] Field of Search ................... 128/200.26, 207.14, 128/207.15

[56] References Cited

U.S. PATENT DOCUMENTS

| | | | |
|---|---|---|---|
| 2,862,498 | 12/1958 | Weekes | 128/207.14 |
| 3,880,168 | 4/1975 | Berman | 128/207.15 |
| 3,884,242 | 5/1975 | Bazell et al. | 128/207.15 |
| 4,056,104 | 11/1977 | Jaffe | 128/207.15 |
| 4,156,428 | 5/1979 | Henkin | 128/207.16 |
| 4,235,239 | 11/1980 | Elam | 128/207.15 |
| 4,488,548 | 12/1984 | Agdanowski | 128/207.15 |
| 5,060,647 | 10/1991 | Alessi | 128/207.14 |
| 5,334,148 | 8/1994 | Martin | 604/96 |
| 5,372,131 | 12/1994 | Heinen, Jr. | 128/207.14 |
| 5,507,284 | 4/1996 | Daneshvar | 128/207.14 |

FOREIGN PATENT DOCUMENTS 2008140  5/1979  United Kingdom .

OTHER PUBLICATIONS

EPO Communication and attached European Search Report, Application No. EP 97 30 8918, EPO Communication dated Sep. 22, 1998, 4 pages.

*Primary Examiner*—Aaron J. Lewis
*Attorney, Agent, or Firm*—Hale and Dorr LLP

[57] ABSTRACT

In its presently preferred form, an endotracheal tube (ET) is shaped to bring its rounded or bevelled distal tip end into the central axis or midline, for ease of passage into the glottic opening and through the region of the vocal cords; the distal-end shaping also involves a laterally and vertically reducing taper that is symmetrical with respect to a vertical plane of symmetry which includes the central axis. Distal-end ports or perforations are in the symmetrically arrayed walls of a triangular section of the tube which at least characterizes the region of tapering section and which conforms with the triangular-shaped space between the vocal cords, for added ease of insertion into the patient's trachea. The reducing taper of the roughly triangular-shaped section extends preferably and optionally to form a wedging fit against vocal cords, with or without the assistance of a conventional inflatable cuff of similar sectional profile.

35 Claims, 4 Drawing Sheets

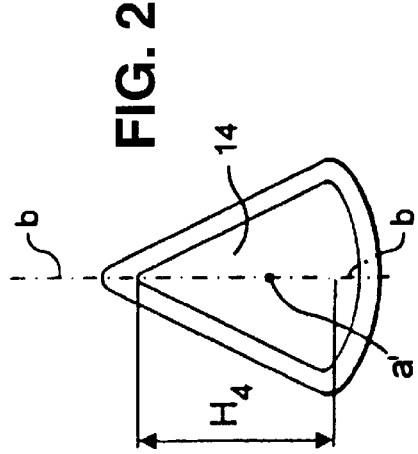
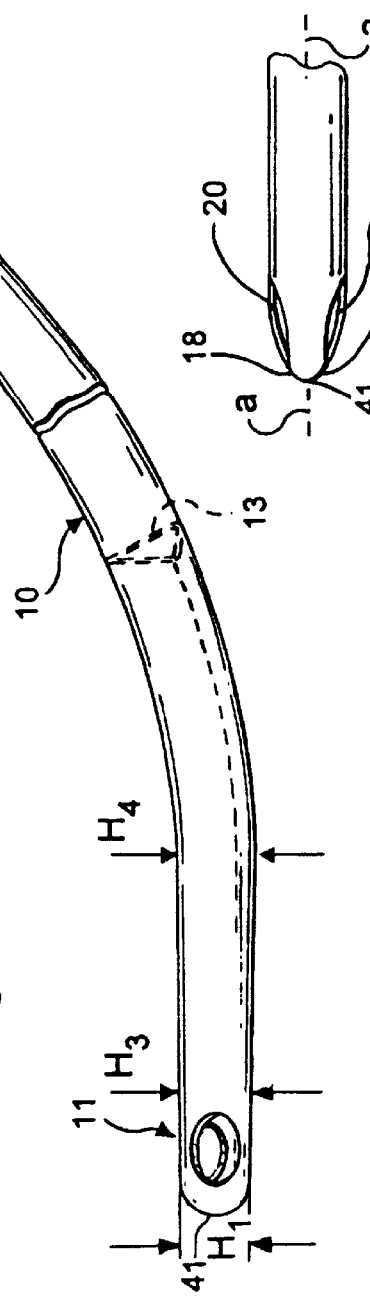
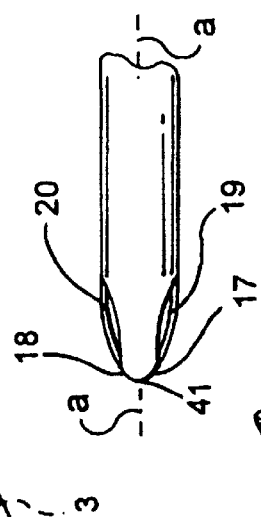
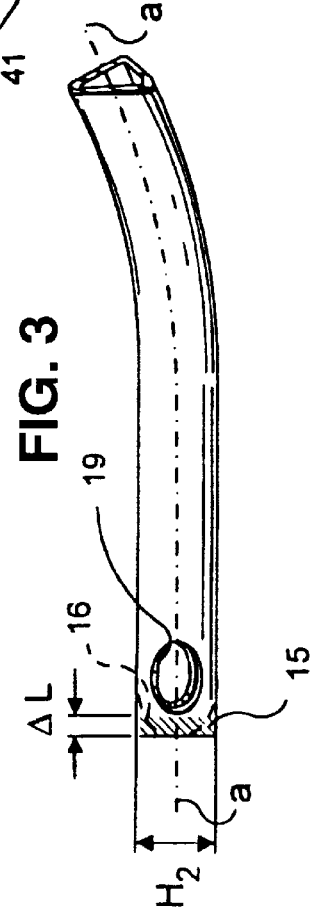

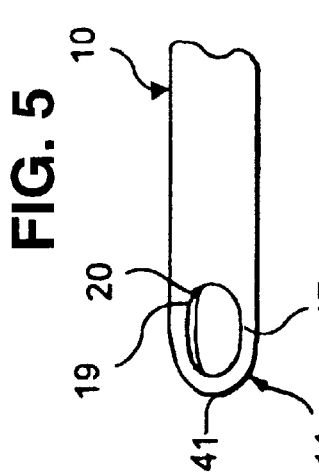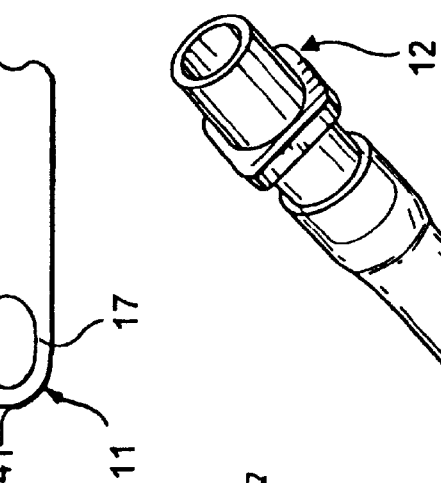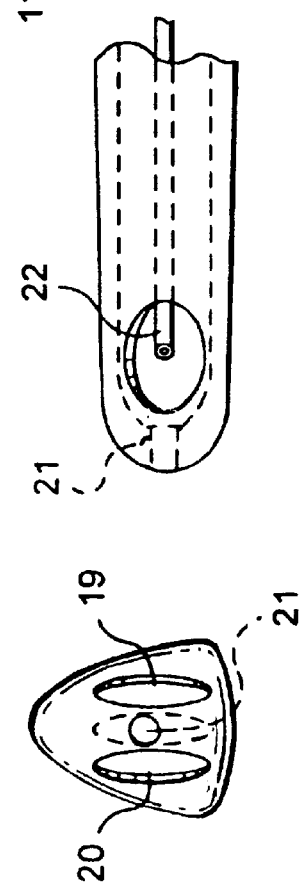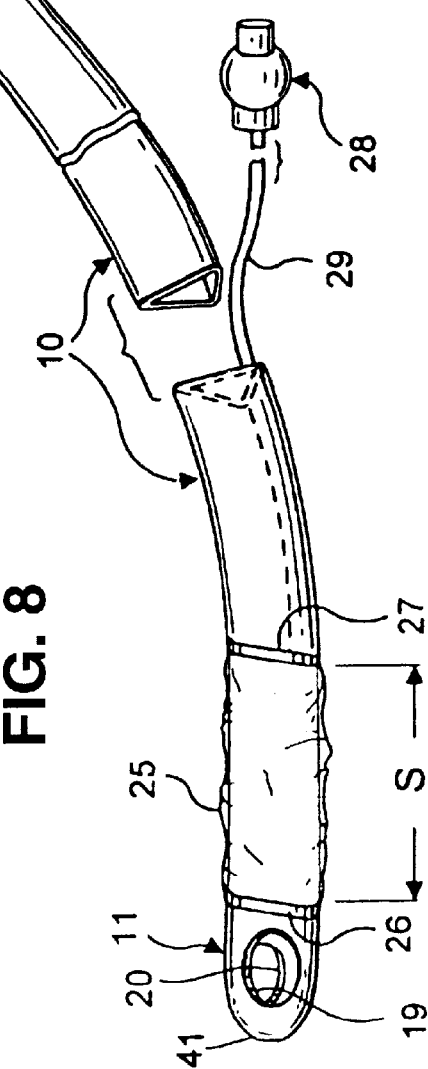

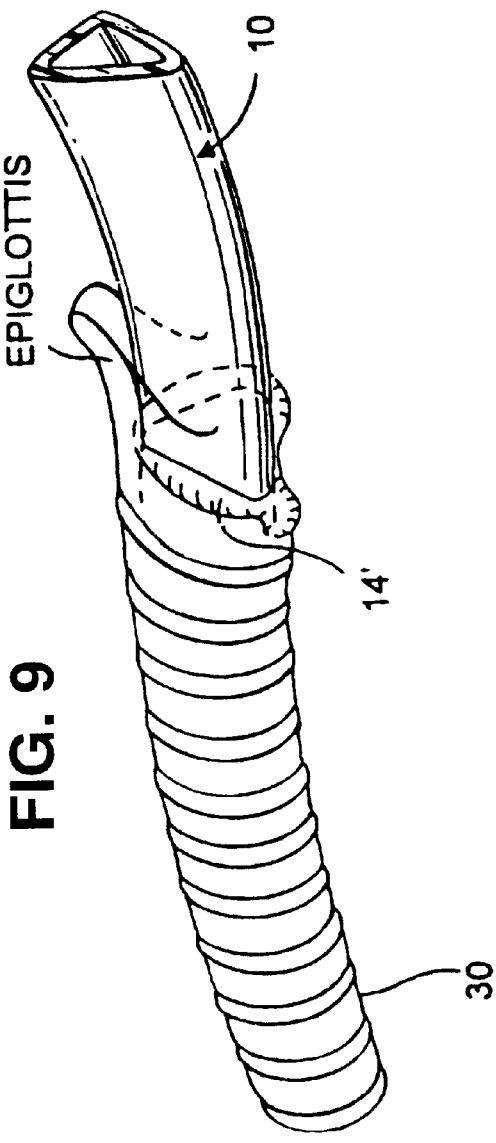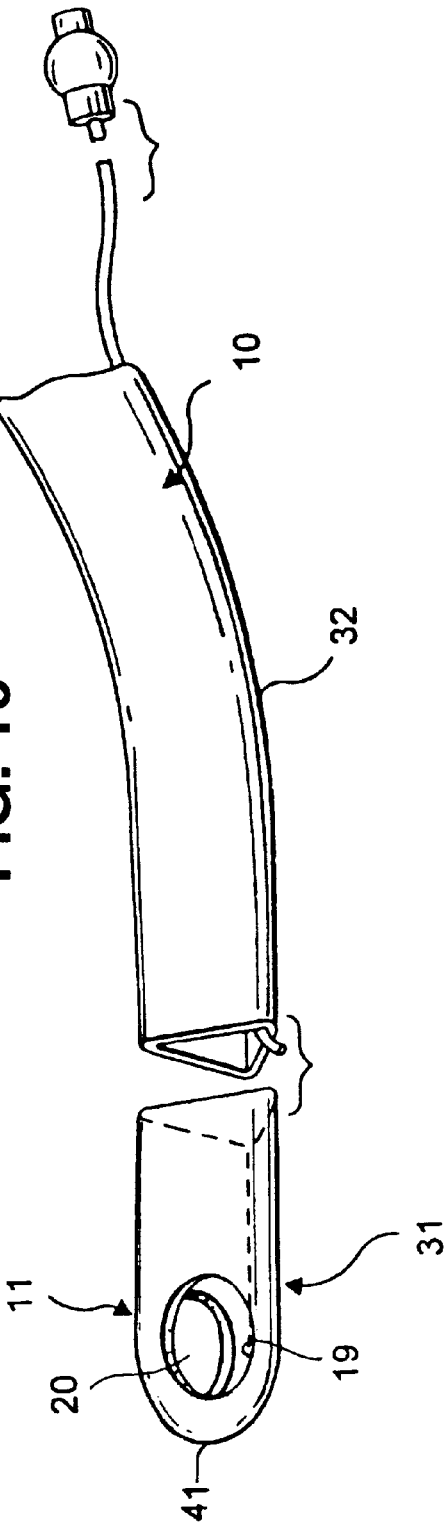

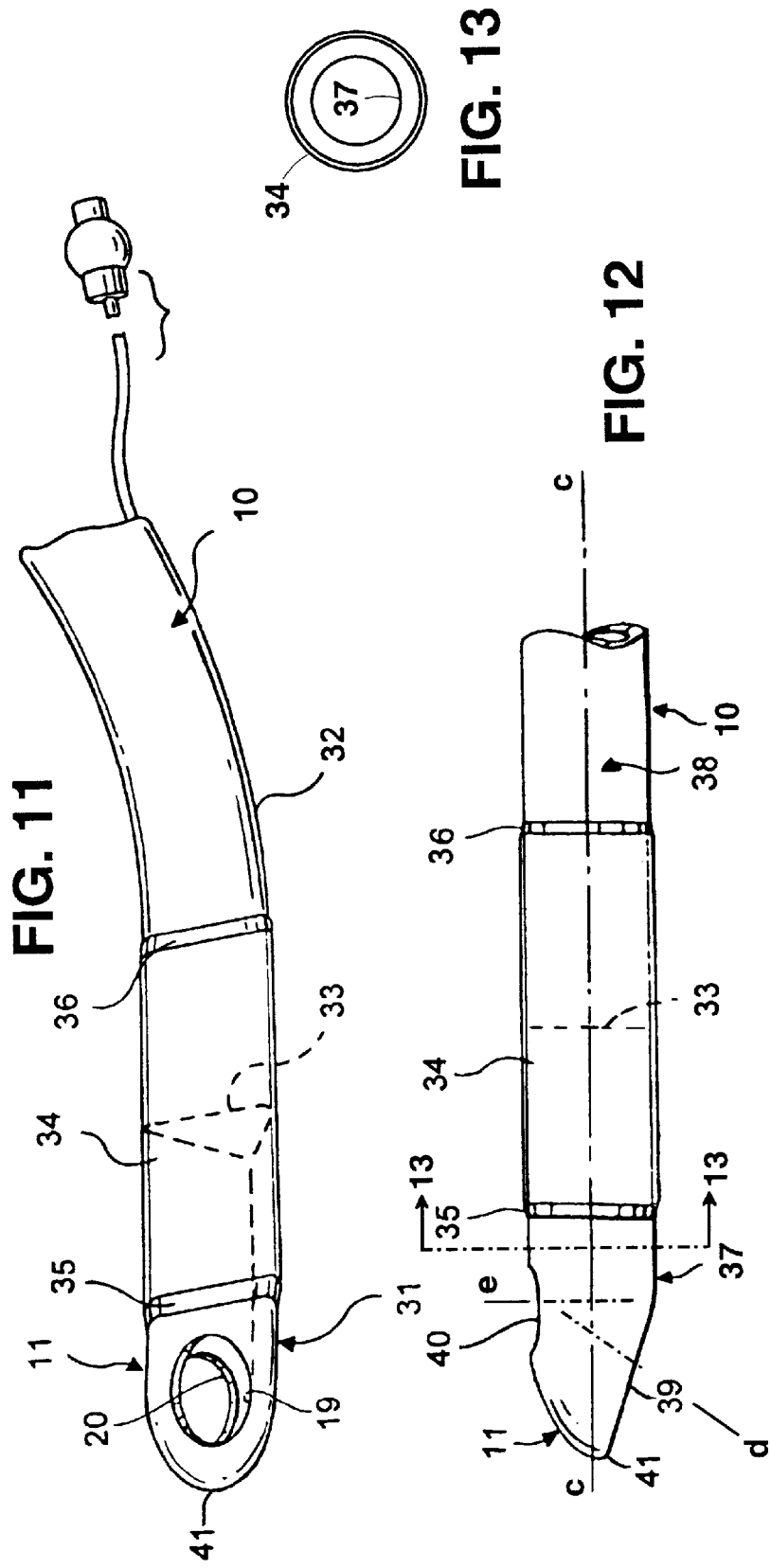

ENDOTRACHEAL TUBE CONSTRUCTION

BACKGROUND OF THE INVENTION

The endotracheal tube is an artificial airway device usually made of plastics or rubber material which consists of a flexible, usually somewhat curved tube, typically of 8-mm internal diameter in adults, with a square-cut outer or proximal end for attachment to a standard 15-mm connector and a bevelled or diagonally-cut opposite or distal end for ease of insertion through the laryngeal aperture (glottis) and into the trachea (windpipe). Normally, an endotracheal tube has hermetically sealed engagement to the walls of the trachea, by reason of a typically cylindrical or spheroidal concentric plastic or rubber cuff fitted to the tube shaft, at some 2 to 3 cm of proximal offset from said bevelled end. Such a cuff is inflated by means of an inflating syringe via an inflation line commonly running in the wall of said tube and continuous with a flexible pilot tube, pilot balloon and spring-loaded check valve; after the endotracheal tube has been installed to the correct depth in the patient's trachea, the cuff is inflated, and the check valve retains the cuff in its inflated state.

A wide variety of such endotracheal tubes are known and in common use throughout the world, and most have in common the features detailed above. Their popularity is due to their ability to provide means of administering anaesthetic gases to the patient's lungs while simultaneously preventing entry into the lungs of potentially lethal gastric juice which may otherwise flood into the airways when the body's protective reflexes have been abolished by the administration of general anaesthesia. However, many complications are known to be caused by the placement of such tubes, whether from trauma of insertion, pressure of the tube lying against the walls of the larynx or pressure exerted on the delicate walls of the trachea by the sealing cuff once inflated. The traditional bevel on an endotracheal tube is in no way designed to fit the slot-shaped and somewhat triangular aperture it must pass through when the tube is inserted, resulting commonly in injury to the larynx due to the bevel tip bruising one or the other side of the larynx during passage. Also, once installed, the circular cross-section of conventional tubes differs from the roughly triangular slotted shape of the laryngeal aperture so that when the vocal cords forming the sidewalls of said triangle contract against this circular shape, stretching and consequent malfunction of the cords commonly occurs. Tubes have been designed, for example some designs of plastic (PVC) tube manufactured by Mallinkrodt (Germany and U.S.A.) in which the bevelled tip is directed away from the tube's side wall, but such tube-bevel design does not bring the leading edge of the bevel into the mid-line of the tube shaft, and the tube is of uniform hardness (typically 80 durometer).

To insert an endotracheal tube in a patient's windpipe, an instrument called a laryngoscope is normally used. This device comprises a light source placed within a blade designed to lift the tongue forwards, revealing the glottic aperture below the posterior surface of the tongue. Endotracheal tubes are normally curved so as to facilitate entry of the bevelled tube tip between the vocal cords once these have been revealed by the laryngoscope. However, this curvature of the tube, while facilitating entry into the glottis, actually causes the tube to scrape against the anterior wall of the windpipe as it passes further into place, because the anatomy of the windpipe curves in the direction opposite to the curvature of the tube. My pending patent application Ser. No. 08/901,055 describes an intubating laryngeal mask, namely, an LMA modified to act as a guide to installing an endotracheal tube; wherein the need to use a laryngoscope can be avoided, while also avoiding the need for the endotracheal tube to be curved. The present invention pertains to an endotracheal tube designed principally for use with an intubating LMA, and the disclosure of said pending patent application is hereby incorporated by reference.

BRIEF STATEMENT OF THE INVENTION

The principal object of the invention is to provide an improved endotracheal tube construction, featuring ease of entry into the glottic opening.

A specific object is to meet the above object with a distal-end configuration which substantially conforms to the sectional profile of the glottic opening.

Another specific object is to meet the above objects with a distal-end element of lesser durometer than that of a conventional endotracheal tube, said element having a proximal end configured for fixed connection to the distal end of a conventional endotracheal tube, and said element having a distal end which is configured for substantial conformance to the sectional profile of the glottic opening.

It is also an object to meet the above objects with an endotracheal tube having a sectional profile which not only conforms at its distal end to the profile of the glottic opening but which also conforms to said profile continuously in the proximal direction, at least to a location of potentially lapped registry with the vocal cords of a patient, in the installed position of the endotracheal tube.

Still another object is to provide an endotracheal tube with a distal-end section adapted for installed sealing conformance to tissues of the vocal-cord region.

Yet another object is to provide an endotracheal tube of the character indicated with a distal end which incorporates radio-opaque means for radiographic identification of installed location in a patient's trachea.

In its preferred embodiment, the invention achieves these objects, along with further features to be described, by providing an endotracheal-tube (ET) construction which is adapted for use with an intubating laryngeal-mask airway (LMA) and wherein the distal end of the ET tube per se is specially formed for ease of entry into a patient's glottic opening. Preferably, at least the distal end of the new ET construction is of elastomeric material (a) that is of less-than-conventional stiffness, for softer and somewhat yielding entry engagement with the glottic opening, (b) that is smoothly and symmetrically formed with narrow width about a vertical plane of symmetry which includes what may be termed the tube axis, as said axis may be said to exist in close approach to the distal end, (c) that progressively broadens in the proximal direction from said end, into a generally triangular section which conforms to the profile of the glottic opening and which is also adapted for sealing or near-sealed relation to the vocal cords, and (d) that, at least for that portion of the distal length of the ET tube which extends from the glottic opening into lapped engagement with the vocal cords, the generally triangular section progressively reduces to the extent of establishing a progressive and effectively sealed closing engagement with the walls of the vocal cords.

Various embodiments are described.

DESCRIPTION OF THE DRAWINGS

In the drawings which show, for illustrative purposes, preferred and other embodiments of the invention:

FIG. 1 is a side view, partially in elevation and partially in perspective, of a preferred endotracheal-tube embodiment of the invention;

FIG. 2 is a front-aspect view, schematically indicative of the shape of a glottic opening;

FIG. 3 is a fragmentary side-aspect view similar to FIG. 1, to illustrate manufacturing steps in fabricating the distal end portion of the endotracheal tube of FIG. 1;

FIG. 4 is an enlarged fragmentary plan view of air/gas porting adjacent the distal end of the endotracheal tube of FIG. 1;

FIG. 5 is an enlarged fragmentary side view of the distal end of FIG. 4;

FIG. 6 is an end view of the distal end of the endotracheal tube of FIGS. 1 and 4, with modification to provide centralizing guidance of a fiber-optic viewing/illuminating device;

FIG. 7 is a view similar to FIG. 5, but additionally showing the FIG. 6 provision for centralizing guidance;

FIG. 8 is a view similar to FIG. 1 to show a modification;

FIG. 9 is a view in perspective to show insertional accommodation of the distal end of an endotracheal tube of FIG. 1 or FIG. 8 in a human trachea, the trachea being schematically featured essentially only by its cartilagineous bands;

FIG. 10 is a side view in partial perspective, showing separate component parts of a modified distal-end construction;

FIG. 11 is a view similar to FIG. 10, to shown an assembled distal end, for the component parts of FIG. 10;

FIG. 12 is a fragmentary distal-end view in side elevation for a further embodiment of the invention; and FIG. 13 is a sectional view of FIG. 12 taken in the plane 13—13 of FIG. 12 showing the cylindrical cross-section of the distal component of the endotracheal tube.

DETAILED DESCRIPTION

FIG. 1 illustrates the currently preferred endotracheal tube (ET) of the invention, and is seen to comprise an elongate flexible tube 10, which may have an initial curvature, between a distal end 11 and a proximal end fitting 12 that is adapted for external connection to conventional gas/air-monitoring and supply equipment available to the anaesthetist.

The mention of curvature between ends 11, 12 is primarily for purposes of having the ET of FIG. 1 be recognized as an ET, because the thinking and practices of anesthetists have long been conditioned by conventional ET devices as having an arcuate appearance; moreover, the arcuate configuration shown can be understood as an arc in a single vertical plane of symmetry, which includes a geometrically central axis, designated a—a in FIG. 4.

As suggested above, it is recommended that the device of FIG. 1 be inserted via an installed intubating LMA, as of the presently preferred rigid-airway nature described in pending application Ser. No. 08/901,055, wherein the total angle of airway bend, is a circular arc of preferably 128 to 131 degrees, between a straight proximal end and a distal ET-launching end, which aims the launched distal end of an ET for short-span directed entry into a patient's glottic opening.

It is a feature of the invention that at least the distal-end portion of the ET of FIG. 1 shall be of generally isosceles-triangular section 13 which converges gradually from a maximum geometric altitude $H_4$ to a reduced intermediate altitude $H_3$, and distally ending with a most-reduced altitude $H_1$; and these triangle altitudes are to be understood in the context of the patient's glottic opening 14 (FIG. 2) having an altitude $H_4$ which is the maximum external altitude of the generally triangular section of ET tube 10, it being noted that the altitude $H_4$ in FIG. 2 substantially coincides with a vertical plane b—b of symmetry of the glottic opening 14, and that this plane b—b of symmetry includes what may be identified as the longitudinally central mid-line or axis a' of the glottic opening. It is also noted, as in FIG. 2, that the term "generally isosceles" applies to the substantial equality of the oppositely inclined sidewalls of the glottic opening but that the third or base side is bowed; as seen in FIG. 2 and also in the frontal aspect profile of FIG. 7. The context for distal-end 11 entry into the patient's glottic opening 14 is therefore one of relatively safe clearance, and thus tolerance for a range of safely directed ET entry into the glottic opening.

The indicated tolerance is aided favorably in terms of avoiding trauma-inducing ET engagement with body tissues in the intubating course of LMA-guided entry into the glottic opening. For example, it is a feature of the invention that the stiffness/hardness of the material of at least the glottis-entering distal end of ET tube 10 shall be materially reduced from the typically 80-durometer hardness which characterizes currently favored ET constructions of constant circular section. In contrast to such conventional practice, the texture of the elastomeric material of the glottis-entering end of tube 10 is substantially softer, e.g., in the range of 55 to 65 durometer, and preferably of 60-durometer hardness.

A further feature of the invention, particularly for enhanced avoidance of trauma upon ET insertional advance into and through the glottic opening, derives from my originally preferred technique of distal-end manufacture. This technique of distal-end formation is illustrated in FIG. 3, wherein a distal increment $\Delta L$ of length is laterally crushed and bonded into substantially flat local conformance with and adoption of the defined vertical plane of symmetry (i.e., a—a in FIG. 4). The crush action necessarily establishes a crushed and bonded closure of the distal end of the ET tube, which in the case of a circular tube will become a diametrical closure of substantially uniform thickness (and vertical extent $H_2 > H_1$), and which in the case of the preferred generally triangular section 13 may become a closure that is of more wedge-shaped section, but symmetrical about the above-noted central vertical plane of symmetry. In FIG. 3, the crushed closure of the distal end of tube 10 is designated by shading 15, and a dashed profile 16 will be understood to suggest a finishing step of abrading or otherwise reducing the distal end of tube 10 to a smoothly rounded finish including a distal tip 41, which is substantially as collectively shown by the distal-end profiles of FIGS. 1, 3, 4, 5 and 7.

The flattened, sealed and rounded distal end 11 will be seen to extend distally forward of the minimum section altitude $H_1$ and to have been reduced from the flattened span $H_2$ which preceded the rounding step. From this flattened, and now also rounded, distal end 11, the opposed sidewalls 17, 18 are seen in FIG. 4 to spread in progressive definition of the intermediate generally triangular-section dimensions which are characterized by the intermediate altitude $H_3$, and with further progressive section enlargement to a maximum altitude $H_4$ of generally triangular-section magnitude, namely at the location of substantial triangular-section conformance to the profile (FIG. 2) of the glottic opening 14. In close adjacency to the distal end, the diverging sidewalls 17, 18 are shown with symmetrically opposed ports in the form of longitudinally elongate oval openings 19, 20 that are best seen in FIGS. 4, 6 and 7, it being noted that in the region between altitudes $H_3$ and $H_4$, the symmetrically opposed walls 17, 18 will have become components of flat surfaces that are adapted for substantial if not total conformance to contacted divergent inner faces of the vocal cords.

FIG. 6 and 7 serve to illustrate that for those who prefer the assurance of optical-fiber illumination and fiberscope distally directional viewing on the local central axis of the distal end 11, a short central bore 21 in the otherwise closed end 11 will serve to stabilize axially central orientation of optical-fiber means 22 inserted via the generally triangular-section passage within ET tube 10. FIG. 7 further shows inner-wall ramp profiling 22', convergent to bore 21, whereby to deflect the distal end of the optical-fiber means 22 into smooth alignment with and guided entry into the central bore 21.

The ET device of FIG. 8 incorporates a modification from the device of FIG. 1, involving a circumferentially continuous sleeve 25 of flexible plastic, peripherally sealed, in longitudinally spaced relation S, between such seals at 26/27 that are designed to fully lap the vocal cords. And inflation/deflation means such as a manually operated piston/cylinder syringe (not shown) will be understood, when connected to a suitable check valve 28, to serve inflation air via flexible means 29 which communicates within tube 10 to the closed volume external to tube 10 but contained within the described flexible sleeve 25. Upon ET tube 10 insertion into and via a patient's glottic opening 14, to the extent of sleeve-25 overlap with the patient's vocal cords, the sealed efficacy of full engagement with the vocal cords is assured by relatively light-pressure inflation of the sleeve via means 28, 29.

FIG. 9 serves as a schematic illustration of trachea reception of either one of the described ET embodiments. It is noted that the angle between the laryngeal inlet and the substantially straight trachea is the reverse of curvature developed or necessitated by laryngoscope-guided curvature of ET passage to the point 14' of glottic-aperture entry.

FIGS. 10 and 11 are respectively illustrative of separate ET components of the same device, namely a distal-end component 31 and a proximal tube component 32, which may integrally extend to a proximal end (not shown) that may be as described for the proximal end means 12 of FIG. 1. The adjacent ends of components 31, 32 confront each other with compatibly matched sectional profiles, which suitably are butt-welded with full peripheral completion of their welded relation, suggested at 33 in FIG. 11. A sleeve 34 of flexible material is seen in FIG. 11 to straddle weld 33 and to be in circumferentially complete bonded connection at its respective ends 35, 36 to the external surface of each of the respective components 31, 32. Optionally, inflation/deflation means, as at 28, 29 in FIG. 8 is provided for sleeve 34 action, but the additional function provided by sleeve 34 is a safety feature, namely, in case of an inadvertent failure of the weld connection 33 while the ET device is installed in a patient. Specifically, in such an unfortunate circumstance, the sleeve 34 provides a longitudinal tie of the severed component connection, and the tie enables safe extraction of the severed parts in a single extracting retraction.

It will be seen that the embodiment of FIGS. 10 and 11 enables the distal-end component to be an injection-moldable item of a softer elastomeric material (e.g., in the range 50 to 70 durometer hardness and preferably about 60-durometer hardness) while the remaining proximally extending component may be of stiffer elastomeric material (e.g., about 80-durometer hardness. Also, for greater radiation-viewing of an ET position in the patient's anatomy, a radio-opaque filler, typically 10 percent barium, as an ingredient mixed with the injection or otherwise molded distal-end component 31, will enable easy identification of ET location, upon radiographic inspection after ET insertion into the patient's trachea.

It will further be seen that for the preferred reducing-taper embodiment of FIG. 1, the construction of tube 10 with a roughly triangular cross-section throughout all of the distal part of the tapering length of the ET tube, and in imitation of the shape of the laryngeal opening, can be such that the vocal cords lie comfortably against walls of the larynx irrespective of the depth to which the ET device is inserted; the triangular, and thus anatomically conforming tube cross-section, opens the possibility of establishing an effective seal, by the close fit of the vocal cords against the distal walls of the ET tube, thus obviating the need for an inflatable cuff. Nevertheless, the use of a distally tapering section throughout the region of ET tube penetration into the trachea is a feature that is not necessarily limited to the preferred triangular section of the distal end of the ET tube. relatively soft elastomeric material, suitably injection-molded, and butt-welded or otherwise secured to the distal end of a second flexible proximal-end component 38 of relatively harder elastomeric material, which may nevertheless be so flexible as to be initially straight but able to adapt itself readily to the curved path of relatively rigid guidance provided by an intubating LMA. Thus, the flexible component 38 may be cylindrical throughout, for conformance with the rigid curvilinear guidance path of the intubating LMA, and at the welding 33 of both components 37, 38 to each other, the cylindrically tubular nature of both components 37, 38 at their interconnection may be of matching or suitably mating cylindrical nature.

The structure of FIG. 12 can be seen as of cylindrical-tube configuration to and through the welded connection 33, and therefore as having cylindrical consistency about a central axis or mid-line c, wherein the convergent distally projecting end is sufficiently rounded and continuous as to contain the mid-line or axis c, despite the fact of a shallow-angle truncation at 39a; truncation 39 will be understood to account for a first side port (39b), approximately 180° removed from the angular location, about axis c, for a second side port 40. The first and second side ports 39b, 40 have respective first and second central axes d, e. Thus, the smoothly continuous contouring of the reduced distal end, about the local mid-line or axis c will be seen as favoring smooth non-traumatising entry into the glottic opening and into the trachea, even though the openings 39a, 40 are differently located and asymmetrically profiled. Finally, as in FIG. 10, a safety sleeve 34 in FIG. 12 is circumferently bonded to components 37, 38 at spaced locations and straddling the connection 33.

What is claimed is:

1. An endotracheal tube construction comprising an axially elongate tube extending between a proximal-end portion adapted for connection to an external source of air/gas supply for anaesthetic service of a patient's lungs, and a distal-end portion of section-conformance to the sectional profile of a patient's glottic opening, said distal-end portion having a convergently tapered distal limit of sectional profile reduced from that of a patient's glottic opening, said distal-end portion being configured for closure such that the closure is peripherally continuous at the location of intersection with the central mid-line or axis of said distal-end portion, said location of intersection coinciding with a distal tip of said distal-end portion such that said distal tip is axially centered relative to the cross-section of said distal-end portion.

2. The construction of claim 1, in which the material at said distal-end portion is substantially more soft than the material of said proximal-end portion.

3. The construction of claim 2, in which distal-end portings are in the material of said distal-end portion and at locations angularly offset from said central mid-line or axis passage through said closure.

4. The construction of claim 1, in which said distal end is configured for closure at a laterally narrow nose formation having symmetry about a vertical plane that includes said central mid-line or axis of the distal-end portion.

5. The construction of claim 1, in which the conforming section is generally isosceles triangular.

6. The construction of claim 1, wherein at least said distal-end portion is of elastomeric material having a durometer hardness in the range 50 to 70.

7. The construction of claim 6, in which said durometer hardness is about 60.

8. The construction of claim 6, in which the entire axially elongate extent of said tube is of said durometer hardness.

9. The construction of claim 6, in which said tube comprises a proximal-end portion of elastomeric material having a durometer hardness of at least substantially 80, said distal-end portion and said proximal-end portion having a region of butt-welded connection to each other.

10. The construction of claim 9, in which a peripherally continuous sleeve of flexible material longitudinally laps the butt-welded region, said sleeve being peripherally secured at its distal end to said distal-end portion, and said sleeve being peripherally secured at its proximal end to said proximal-end portion.

11. The construction of claim 10, in which said sleeve is free of connection to said tube portions for a longitudinal span that more than laps said region of butt-welded connection.

12. The construction of claim 10, in which inflation/deflation means for said sleeve includes a separate passage within said proximal-end portion and flexible means communicating with said passage and external of said proximal-end portion for inflation/deflation control of said sleeve.

13. An endotracheal tube construction comprising an axially elongate tube extending between a proximal-end portion adapted for connection to an external source of air/gas supply for anaesthetic service of a patient's lungs, and a distal-end portion of section-conformance to the sectional profile of a patient's glottic opening, said distal-end portion having a convergently tapered distal limit of sectional profile reduced from that of a patient's glottic opening, in which the conforming section is generally triangular, with progressing section scale, wherein the section scale reduces in the distal direction.

14. The construction of claim 13, in which the generally triangular section defines two like sidewalls that are symmetrically disposed about a vertical plane which includes the central axis of the tube, and at least one side port in each of said sidewalls and near but short of the distal limit of said distal end.

15. An endotracheal tube construction comprising an elongate tube extending between a proximal-end portion adapted for connection to an external source of air/gas supply for anaesthetic service of a patient's trachea, and a distal-end portion adapted for entry via a patient's glottic opening and into a patient's trachea and beyond a region of longitudinal overlap with a patient's vocal cords, said distal-end portion having a distal-tip end of reduced section that is less than that of a patient's glottic opening, and said section expanding progressively in the proximal direction and with generally triangular configuration throughout at least the longitudinal region of lap of a patient's vocal cords and of a patient's glottic opening, said generally isosceles-triangular configuration defining like sidewalls on opposite sides of a central plane of vertical symmetry of said distal-end portion, and at least one open port in each of said sidewalls beyond the region of vocal-cord overlap and short of the distal limit of said distal-tip end.

16. The construction of claim 15, in which said sidewalls have an included angle of 30 to 45 degrees divergence and are scaled at the region of vocal-cord overlap for substantially complete engagement with a patient's vocal cords in an intermediate position between normal and deep inspiration.

17. The construction of claim 16, in which the included angle is substantially 40 degrees.

18. The construction of claim 16, in which said sidewalls have an included angle of 30 to 45 degrees divergence and are scaled at the region of glottic-opening overlap for substantially complete engagement with a patient's glottic opening.

19. The construction of claim 18, in which the included angle is substantially 40 degrees.

20. The construction of claim 15, in which at least said distal-end portion is of elastomeric material having a durometer-hardness in the range 55 to 65.

21. The construction of claim 20, in which the durometer hardness is substantially 60.

22. The construction of claim 15, in which at least the distal-end portion is of elastomeric material containing a radio-opaque filler.

23. The construction of claim 15, further comprising a peripherally continuous inflatable/deflatable cuff carried by said distal-end portion at the region of longitudinal overlap with a patient's vocal cords.

24. The construction of claim 15, in which said elongate tube has a centrally located geometric longitudinal axis which terminates at said distal-tip end with a longitudinal bore that is sized for guidance and axially central orientation of the distal end of optical-fiber viewing means that is insertable within said elongate tube, the interior profile of walls of said triangular configuration having a distally convergent guidance-ramp formation that is adapted to pilot the advancing distal end of said viewing means for centralizing approach to and for smooth entry into centrally guided relation with said longitudinal bore.

25. An endotracheal tube construction comprising an axially elongate tube extending between a proximal-end portion adapted for connection to an external source of air/gas supply for anaesthetic service of a patient's lungs, said proximal-end portion being of relatively hard material which is nevertheless flexibly adapted to guided curvature via an intubating LMA, and a distal-end tubular portion of relatively soft flexible material having a distally forwardly projecting tip end, said distal-end portion having a convergently tapered distal limit of sectional profile reduced from that of a patient's glottic opening and having a geometric central midline or axis which intersects and traverses said tip end, said distal-end portion being configured for closure such that the closure is peripherally continuous at the location of intersection with said central midline or axis of said distal-end portion, said location of intersection coinciding with a distal tip of said distal-end portion such that said distal tip is axially centered relative to the cross-section of said distal-end portion.

26. An endotracheal tube construction comprising an axially elongate tube extending between a proximal end adapted for connection to an external source of air/gas supply for anaesthetic service of a patient's lungs, and a distal-end portion configured for closure such that the closure is peripherally continuous at the location of intersection with the central mid-line or axis of said distal-end portion, said location of intersection coinciding with a distal tip of said distal-end portion such that said distal tip is axially centered relative to the cross-section of said distal-end portion.

27. The construction of claim 26, wherein said tube comprises a proximal-end portion between said proximal end and said distal-end portion, said distal-end portion and the adjoining section of said proximal-end portion having cylindrical cross-sections.

28. The construction of claim 26, wherein said distal-end portion has a convergently tapered distal limit of sectional profile reduced from that of a patient's glottic opening.

29. The construction of claim 26, wherein said distal-end portion has a sidewall having an outer surface contained in a sidewall plane which intersects a vertical plane including the central mid-line or axis of said distal-end portion, said sidewall being longitudinally inclined such that an acute angle is defined between said sidewall and vertical planes, said sidewall containing a first side port.

30. The construction of claim 29, wherein said distal-end portion contains a second side port offset from said sidewall.

31. The construction of claim 30, wherein said first and second side ports are asymmetrically profiled.

32. The construction of claim 30, wherein said first and second side ports have respective first and second central axes, said second side port being oriented relative to said sidewall such that said first and second central axes are contained in a plane which is generally perpendicular to said vertical plane.

33. The construction of claim 32, wherein said second side port is oriented relative to said sidewall such that said first central axis intersects said second central axis, said second side port being further oriented relative to said sidewall such that an acute angle is defined between said first and second central axes.

34. The construction of claim 26, wherein said tube comprises a proximal-end portion between said proximal end and said distal-end portion, said proximal-end portion having an end-to-end abutting relation to said distal-end portion in a region of abutting connection, and further comprising a peripherally continuous sleeve of flexible material which longitudinally laps said region of abutting connection, said sleeve having a distal end peripherally secured to said distal-end portion, said sleeve having a proximal end peripherally secured to said proximal-end portion.

35. The construction of claim 34, in which said proximal and distal ends of said sleeve are longitudinally offset from said region of abutting connection such that said sleeve is free of connection to said distal- and proximal-end portions for a longitudinal span that more than laps said region of abutting connection.

* * * * *